(12) United States Patent
Yamago et al.

(10) Patent No.: US 7,662,899 B2
(45) Date of Patent: Feb. 16, 2010

(54) ORGANIC TELLURIUM COMPOUND, PROCESS FOR PRODUCING THE SAME, LIVING RADICAL POLYMERIZATION INITIATOR, PROCESS FOR PRODUCING POLYMER WITH THE SAME, AND POLYMER

(75) Inventors: Shigeru Yamago, Kyoto (JP); Junichi Yoshida, Hirakata (JP)

(73) Assignee: Otsuka Chemical Co., Ltd., Osaka (JP)

( * ) Notice: Subject to any disclaimer, the term of this patent is extended or adjusted under 35 U.S.C. 154(b) by 269 days.

(21) Appl. No.: 11/878,901

(22) Filed: Jul. 27, 2007

(65) Prior Publication Data

US 2008/0004366 A1 Jan. 3, 2008

Related U.S. Application Data

(62) Division of application No. 10/523,824, filed as application No. PCT/JP02/08003 on Aug. 6, 2002, now Pat. No. 7,276,569.

(51) Int. Cl.
C08F 12/02 (2006.01)
C08C 395/00 (2006.01)
C08F 2/46 (2006.01)

(52) U.S. Cl. ............... 526/343; 522/49; 528/403; 528/407; 562/899

(58) Field of Classification Search ............ 525/242; 528/403, 407, 408; 526/323, 319, 343; 562/899; 522/49
See application file for complete search history.

(56) References Cited

U.S. PATENT DOCUMENTS

2002/0061991 A1  5/2002  Charmot et al.

OTHER PUBLICATIONS

Yamago et al. "Tailored Synthesis of Structurally Defined polymers by Organotellurium-Mediated Living Radical Polymerization: Synthesis of Poly(meth)acrylate Derivatives and Their Di- and Triblock Copolymers", Journal of American Chemical Society, 2002, 124, 13666-13667.*

Kanda et al. "Generation of allyl- and benzyllithiums from the corresponding halides by the aid of lithium-tellurium exchange reactions", Journal of Organometallic Chemistry, 473 (1994), 71-83.*

Lars Engman et al., "Toward Novel Antioxidants: Preparation of Dihydrotellurophenes and Selenophenes by Alkyltelluride-Mediated Tandem $S_{RN}1/S_{H}i$ Reactions", Journal of Organic Chemistry, vol. 64, pp. 6764-6770, XP002352862, 1999.

Melissa J. Laws et al., "Intramolecular Homolytic Substitution at Tellurium: Preparation of a Dihydrotellurophene by Alkyltelluride-Mediated $S_{RN}1/S_{H}i$ Reactions", Tetrahedron Letters, vol. 38, No. 48, pp. 8429-8432, 1997.

Shigeru Yamago et al., "Organotellurium Compounds as Novel Initiators for Controlled/Living Radical Polymerizations. Synthesis of Functionalized Polystyrenes and End-Group Modification", Journal of the American Chemical Society, 124(12), pp. 2874-2875, 2002, Mar. 27, 2002.

Takahiro Kanda et al., "Generation of allyl- and benzyllithiums from the corresponding halides by the aid of lithium-tellurium exchange reactions", Journal of Organometallic Chemistry, 473(1-2), pp. 71-83 (1994).

Mary Ann Wagner et al., "Monomeric Sarcosine Oxidase: 1. Flavin Reactivity and Active Site Binding Determinants", Biochemistry, 39(30), pp. 8813-8824, 2000.

Li-Biao Han et al., "Carbotelluration of alkynes", Journal of the American Chemical Society, 114(19), pp. 7591-7592, 1992.

Louis A. Silks, III et al., "Synthesis and $^{125}$Te NMR Spectroscopy of α-Tellurocarbonyl compounds and derivatives", Synthetic Communications, 21(8-9), pp. 1105-1119, 1991.

Yuqing Ho et al., "A New Synthesis of α-aryltelluro esters", Synthetic Communications, 19(9-10), pp. 1625-1629, 1989.

* cited by examiner

*Primary Examiner*—David Wu
*Assistant Examiner*—Michael M Bernshteyn
(74) *Attorney, Agent, or Firm*—Wenderoth, Lind & Ponack, L.L.P.

(57) ABSTRACT

An organotellurium compound of the formula (1) is useful as a living radical polymerization initiator and makes possible precision control of molecular weights and molecular weight distributions under mild conditions (1)

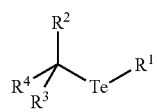

wherein $R^1$ is $C_1$-$C_8$ alkyl, $R^2$ and $R^3$ are each a hydrogen atom or $C_1$-$C_8$ alkyl, and $R^4$ is aryl, substituted aryl, aromatic heterocyclic group, hydroxycarbonyl or cyano.

11 Claims, No Drawings

ORGANIC TELLURIUM COMPOUND, PROCESS FOR PRODUCING THE SAME, LIVING RADICAL POLYMERIZATION INITIATOR, PROCESS FOR PRODUCING POLYMER WITH THE SAME, AND POLYMER

This application is a Divisional application of Ser. No. 10/523,824, filed Feb. 4, 2005, now U.S. Pat. No. 7,276,569, which is a National Stage Application of PCT/JP2002/008003 filed Aug. 6, 2002.

TECHNICAL FIELD

The present invention relates to organotellurium compounds and a process for preparing the same. More particularly, the invention relates to living radical polymerization initiators of the tellurium type, processes for preparing macro living radial polymerization initiators, living radical polymers and block polymers with use of the initiator, and these macro living radical polymerization initiators and polymers.

BACKGROUND ART

Living radical polymerization is a polymerization process which is adapted for precision control of molecular structures while ensuring convenience and universal usefulness of radical polymerization, and is powerful means for preparing novel polymer materials. Georges et al has made a report on a typical example of living radical polymerization using TEMPO (2,2,6,6-tetramethyl-1-piperidinyloxy) as an initiator (publication of JP-A No. 1994-199916).

This process makes it possible to control molecular weights and molecular weight distributions, but requires a high polymerization temperature of 130° C. and is difficult to use for monomers having a thermally unstable functional group. The process is also unsuited to the control of modification of terminal functional groups of high molecular weight compounds.

An object of the present invention is to provide an organotellurium compound which is useful as a living radical polymerization initiator and which makes possible precision control of molecular weights and molecular weight distributions (PD=Mw/Mn) under mild conditions, a process for preparing the compound, a process for producing a polymer with use of the compound, and the polymer.

DISCLOSURE OF THE INVENTION

The present invention provides an organotellurium compound represented by the formula (1)

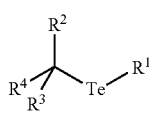

(1)

wherein $R^1$ is $C_1$-$C_8$ alkyl, $R^2$ and $R^3$ are each a hydrogen atom or $C_1$-$C_8$ alkyl, and $R^4$ is aryl, substituted aryl, aromatic heterocyclic group, hydroxycarbonyl or cyano.

The invention provides a process for preparing an organotellurium compound represented by the formula (1) characterized by reacting a compound represented by the formula (2), a compound represented by the formula (3) and metallic tellurium

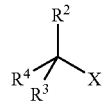

(2)

wherein $R^2$, $R^3$ and $R^4$ are as defined above, and X is a halogen atom

$M(R^1)m$ (3)

wherein $R^1$ is as defined above, M is an alkali metal, alkaline earth metal or copper atom, and m is 1 when M is an alkali metal, m is 2 when M is an alkaline earth metal, or m is 1 or 2 when M is a copper atom.

The invention provides an organotellurium compound represented by the formula (1) which is obtainable by reacting a compound represented by the formula (2), a compound represented by the formula (3) and metallic tellurium.

The invention provides a living radical polymerization initiator represented by the formula (4)

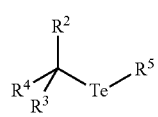

(4)

wherein $R^2$ to $R^4$ are as defined above, and $R^5$ is $C_1$-$C_8$ alkyl, aryl, substituted aryl or aromatic heterocyclic group.

The invention provides a process for producing a living radical polymer characterized by polymerizing a vinyl monomer with use of a compound of the formula (4) as a living radical polymerization initiator.

The invention provides a living radical polymer which is obtainable by subjecting a vinyl monomer to living radical polymerization with use of a living radical polymerization initiator of the formula (4).

The invention provides a macro living radical polymerization initiator (macroinitiator) comprising the living radical polymer.

The present invention provides a process for producing a block copolymer characterized in that a vinyl monomer is polymerized using the macro living radical polymerization initiator (macroinitiator) as a living radical polymerization initiator.

The invention provides a block copolymer which is obtainable by polymerizing a vinyl monomer using the macro living radical polymerization initiator (macroinitiator) as a living radical polymerization initiator.

Organotellurium compounds of the present invention are represented by the formula (1)

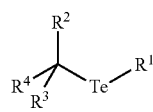

(1)

wherein $R^1$ is $C_1$-$C_8$ alkyl, $R^2$ and $R^3$ are each a hydrogen atom or $C_1$-$C_8$ alkyl, and $R^4$ is aryl, substituted aryl, aromatic heterocyclic group, hydroxycarbonyl or cyano.

Examples of groups represented by $R^1$ are as follows.

Examples of $C_1$-$C_8$ alkyl groups usable are straight-chain, branched chain or cyclic alkyl groups having 1 to 8 carbon atoms, such as methyl, ethyl, n-propyl, isopropyl, cyclopropyl, n-butyl, sec-butyl, tert-butyl, cyclobutyl, n-pentyl, n-hexyl, n-heptyl and n-octyl. Preferable alkyl groups are straight-chain or branched chain alkyl groups having 1 to 4 carbon atoms. Methyl or ethyl is more preferable.

Examples of groups represented by $R^2$ and $R^3$ are as follows.

Examples of $C_1$-$C_8$ alkyl groups usable are the same as the alkyl groups represented by $R^1$ and given above.

Examples of groups represented by $R^4$ are as follows.

Examples of groups usable include aryl groups such as phenyl and naphthyl, substituted aryl groups such as phenyl having a substituent and naphthyl having a substituent, and aromatic heterocyclic groups such as pyridyl, furyl and thienyl. Examples of substituents of aryl groups having a substituent are a halogen atom, hydroxyl, alkoxyl, amino, nitro, cyano, carbonyl-containing groups represented by —$COR^6$ ($R^6$=$C_1$-$C_8$ alkyl, aryl, $C_1$-$C_8$ alkoxyl or aryloxy), sulfonyl, trifluoromethyl, etc. Preferable aryl groups are phenyl and trifluoromethyl-substituted phenyl. Preferably such substituted groups have one or two substituents at the para-position or ortho-position.

Examples of preferred hydroxycarbonyl groups are those represented by —$COOR^7$ ($R^7$=H, $C_1$-$C_8$ alkyl or aryl) such as carboxyl, methoxycarbonyl, ethoxycarbonyl, propoxycarbonyl, n-butoxycarbonyl, sec-butoxycarbonyl, tert-butoxycarbonyl, n-pentoxycarbonyl and phenoxycarbonyl. Methoxycarbonyl and ethoxycarbonyl are more desirable hydroxycarbonyl groups.

Examples of organotellurium compounds represented by the formula (1) are as follows.

Such organotellurium compounds are preferably (methyltellanyl-methyl)benzene, (1-methyltellanyl-ethyl)benzene, (2-methyltellanyl-propyl)benzene, 1-chloro-4-(methyltellanyl-methyl)benzene, 1-hydroxy-4-(methyltellanyl-methyl)benzene, 1-methoxy-4-(methyltellanyl-methyl)benzene, 1-amino-4-(methyltellanyl-methyl)benzene, 1-nitro-4-(methyltellanyl-methyl)benzene, 1-cyano-4-(methyltellanyl-methyl)benzene, 1-methylcarbonyl-4-(methyltellanyl-methyl)benzene, 1-phenylcarbonyl-4-(methyltellanyl-methyl)benzene, 1-methoxycarbonyl-4-(methyltellanyl-methyl)benzene, 1-phenoxycarbonyl-4-(methyltellanyl-methyl)benzene, 1-sulfonyl-4-(methyltellanyl-methyl)benzene, 1-trifluoromethyl-4-(methyltellanyl-methyl)benzene, 1-chloro-4-(1-methyltellanyl-ethyl)benzene, 1-hydroxy-4-(1-methyltellanyl-ethyl)benzene, 1-methoxy-4-(1-methyltellanyl-ethyl)benzene, 1-amino-4-(1-methyltellanyl-ethyl)benzene, 1-nitro-4-(1-methyltellanyl-ethyl)benzene, 1-cyano-4-(1-methyltellanyl-ethyl)benzene, 1-methylcarbonyl-4-(1-methyltellanyl-ethyl)benzene, 1-phenylcarbonyl-4-(1-methyltellanyl-ethyl)benzene, 1-methoxycarbonyl-4-(1-methyltellanyl-ethyl)benzene, 1-phenoxycarbonyl-4-(1-methyltellanyl-ethyl)benzene, 1-sulfonyl-4-(1-methyltellanyl-ethyl)benzene, 1-trifluoromethyl-4-(1-methyltellanyl-ethyl)benzene, 1-chloro-4-(2-methyltellanyl-ethyl)benzene, 1-hydroxy-4-(2-methyltellanyl-propyl)benzene, 1-methoxy-4-(2-methyltellanyl-propyl)benzene, 1-amino-4-(2-methyltellanyl-propyl)benzene, 1-nitro-4-(2-methyltellanyl-propyl)benzene, 1-cyano-4-(2-methyltellanyl-propyl)benzene, 1-methylcarbonyl-4-(2-methyltellanyl-propyl)benzene, 1-phenylcarbonyl-4-(2-methyltellanyl-propyl)benzene, 1-methoxycarbonyl-4-(2-methyltellanyl-propyl)benzene, 1-phenoxycarbonyl-4-(2-methyltellanyl-propyl)benzene, 1-sulfonyl-4-(2-methyltellanyl-propyl)benzene, 1-trifluoromethyl-4-(2-methyltellanyl-propyl)benzene, 2-(methyltellanyl-methyl)pyridine, 2-(1-methyltellanyl-ethyl)pyridine, 2-(2-methyltellanyl-propyl)pyridine, methyl 2-methyltellanyl-ethanate, methyl 2-methyltellanyl-propionate, methyl 2-methyltellanyl-2-methylpropionate, ethyl 2-methyltellanyl-ethanate, ethyl 2-methyltellanyl-propionate, ethyl 2-methyltellanyl-2-methylpropionate, 2-methyltellanylacetonitrile, 2-methyltellanyl-propionitrile, 2-methyl-2-methyltellanyl-propionitrile, etc. Preferable are (methyltellanyl-methyl)benzene, (1-methyltellanyl-ethyl)benzene, (2-methyltellanyl-propyl)benzene, methyl 2-methyltellanyl-2-methylpropionate, ethyl 2-methyltellanyl-2-methylpropionate, 2-methyltellanylpropionitrile and 2-methyl-2-methyltellanylpropionitrile.

The organotellurium compound represented by the formula (1) can be prepared by reacting a compound of the formula (2), a compound of the formula (3) and metallic tellurium.

Examples of compounds represented by the formula (2) are as follows.

wherein $R^2$, $R^3$ and $R^4$ are as defined above, and X is a halogen atom.

Examples of groups represented by $R^2$, $R^3$ and $R^4$ are as given above.

Examples of groups represented by X can be a halogen atom such as fluorine, chlorine, bromine or iodine. Chlorine and bromine are preferable.

Examples of compounds usable are benzyl chloride, benzyl bromide, 1-chloro-1-phenylethane, 1-bromo-1-phenylethane, 2-chloro-2-phenylpropane, 2-bromo-2-phenylpropane, p-chlorobenzyl chloride, p-hydroxybenzyl chloride, p-methoxybenzyl chloride, p-aminobenzyl chloride, p-nitrobenzyl chloride, p-cyanobenzyl chloride, p-methylcarbonylbenzyl chloride, phenylcarbonylbenzyl chloride, p-methoxycarbonylbenzyl chloride, p-phenoxycarbonylbenzyl chloride, p-sulfonylbenzyl chloride, p-trifluoromethylbenzyl chloride, 1-chloro-1-(p-chlorophenyl)ethane, 1-bromo-1-(p-chlorophenyl)ethane, 1-chloro-1-(p-hydroxyphenyl)ethane, 1-bromo-1-(p-hydroxyphenyl)-ethane, 1-chloro-1-(p-methoxyphenyl)ethane, 1-bromo-1-(p-methoxyphenyl)ethane, 1-chloro-1-(p-aminophenyl)ethane, 1-bromo-1-(p-aminophenyl)ethane, 1-chloro-1-(p-nitrophenyl)ethane, 1-bromo-1-(p-nitrophenyl)ethane, 1-chloro-1-(p-cyanophenyl)ethane, 1-bromo-1-(p-cyanophenyl)ethane, 1-chloro-1-(p-methylcarbonylphenyl)ethane, 1-bromo-1-(p-methylcarbonylphenyl)ethane, 1-chloro-1-(p-phenylcarbonylphenyl)ethane, 1-bromo-1-(p-phenylcarbonylphenyl)-ethane, 1-chloro-1-(p-methoxycarbonylphenyl)ethane, 1-bromo-1-(p-methoxycarbonylphenyl)ethane, 1-chloro-1-(p-phenoxycarbonylphenyl)-ethane, 1-bromo-1-(p-phenoxycarbonylphenyl)ethane, 1-chloro-1-(p-sulfonylphenyl)ethane, 1-bromo-1-(p-sulfonylphenyl)ethane, 1-chloro-1-(p-trifluoromethylphenyl)ethane, 1-bromo-1-(p-trifluoromethylphenyl)ethane, 2-chloro-2-(p-chlorophenyl)propane, 2-bromo-2-(p-chlorophenyl)propane, 2-chloro-2-(p-hydroxyphenyl)-propane, 2-bromo-2-(p-hydroxyphenyl)propane, 2-chloro-2-(p-methoxyphenyl)propane, 2-bromo-2-(p-methoxyphenyl)propane, 2-chloro-2-(p-aminophenyl)propane, 2-bromo-2-

(p-aminophenyl)propane, 2-chloro-2-(p-nitrophenyl)propane, 2-bromo-2-(p-nitrophenyl)-propane, 2-chloro-2-(p-cyanophenyl)propane, 2-bromo-2-(p-cyanophenyl)propane, 2-chloro-2-(p-methylcarbonylphenyl)propane, 2-bromo-2-(p-methylcarbonylphenyl)propane, 2-chloro-2-(p-phenylcarbonylphenyl)propane, 2-bromo-2-(p-phenylcarbonylphenyl)-propane, 2-chloro-2-(p-methoxycarbonylphenyl)propane, 2-bromo-2-(p-methoxycarbonylphenyl)propane, 2-chloro-1-(p-phenoxycarbonylphenyl)propane, 2-bromo-2-(p-phenoxycarbonylphenyl)propane, 2-chloro-2-(p-sulfonylphenyl)propane, 2-bromo-2-(p-sulfonylphenyl)propane, 2-chloro-2-(p-trifluoromethylphenyl)propane, 2-bromo-2-(p-trifluoromethylphenyl)propane, 2-(chloromethyl)pyridine, 2-(bromomethyl)pyridine, 2-(1-chloroethyl)pyridine, 2-(1-bromoethyl)pyridine, 2-(2-chloropropyl)pyridine, 2-(2-bromopropyl)pyridine, methyl 2-chloroethanoate, methyl 2-bromoethanoate, methyl 2-chloropropionate, methyl 2-bromoethanoate, methyl 2-chloro-2-methylpropionate, methyl 2-bromo-2-methylpropionate, ethyl 2-chloroethanoate, ethyl 2-bromoethanoate, ethyl 2-chloropropionate, ethyl 2-bromoethanoate, ethyl 2-chloro-2-ethylpropionate, ethyl 2-bromo-2-ethylpropionate, 2-chloroacetonitrile, 2-bromoacetonitrile, 2-chloropropionitrile, 2-bromopropionitrile, 2-chloro-2-methylpropionitrile, 2-bromo-2-methylpropionitrile, etc.

Examples of compounds represented by the formula (3) are as follows.

wherein $R^1$ is as defined above, M is an alkali metal, alkaline earth metal or copper atom, and m is 1 when M is an alkali metal, m is 2 when M is an alkaline earth metal, or m is 1 or 2 when M is a copper atom.

Examples of groups represented by $R^1$ are as given above.

Examples of metals represented by M are lithium, sodium, potassium and like alkali metals, magnesium, calcium and like alkaline earth metals, and copper. Lithium is desirable.

Examples of compounds usable are methyllithium, ethyllithium, n-butyllithium, etc.

Next, a detailed description will be given of the process for preparing the compound.

Metallic tellurium is suspended in a solvent. Examples of solvents usable are dimethylformamide (DMF), tetrahydrofuran (THF) and like polar solvents, toluene, xylene and like aromatic solvents, hexane and like aliphatic hydrocarbons, dialkyl ethers and like ethers, etc. THF is preferable. The amount of solvent to be used, which is suitably adjusted, is 5 to 10 ml, preferably 7 to 8 ml, per gram of metallic tellurium.

A compound (3) is slowly added dropwise to the suspension, followed by stirring. The reaction time differs with the reaction temperature and pressure and is usually 5 minutes to 24 hours, preferably 10 minutes to 2 hours. The reaction temperature is −20° C. to 80° C., preferably 15° C. to 40° C., more preferably room temperature. The reaction is conducted usually under atmospheric pressure, but may be conducted at increased pressure or in a vacuum.

Next, a compound (2) is added to the reaction mixture, followed by stirring. The reaction time differs with the reaction temperature and pressure and is usually 5 minutes to 24 hours, preferably 10 minutes to 2 hours. The reaction temperature is −20° C. to 80° C., preferably 15° C. to 40° C., more preferably room temperature. The reaction is conducted usually under atmospheric pressure, but may be conducted at increased pressure or in a vacuum.

The proportions of the compound (2) and compound (3) to metallic tellurium are 0.5 to 1.5 mole of the compound (2) and 0.5 to 1.5 moles of the compound (3), preferably 0.8 to 1.2 moles of the compound (2) and 0.8 to 1.2 mole of the compound (3), per mole of metallic tellurium.

After the completion of the reaction, the solvent is concentrated, and the desired compound is isolated and purified. Although the method of purification can be determined suitably depending on the compound, vacuum distillation or recrystallization is usually preferable.

The living radical polymerization initiator of the invention is a compound represented by the formula (4).

wherein $R^2$ to $R^4$ are as defined above, and $R^5$ is $C_1$-$C_8$ alkyl, aryl, substituted aryl or aromatic heterocyclic group.

Examples of alkyl groups represented by $R^5$ can be the same as the alkyl groups represented by $R^1$ and given above.

Examples of aryl groups, substituted aryl groups and aromatic heterocyclic groups can be the same as those represented by $R^4$ and exemplified above.

Examples of living radical polymerization initiators represented by the formula (4) are (phenyltellanyl-methyl)benzene, (1-phenyltellanyl-ethyl)benzene, (2-phenyltellanylpropyl)benzene, etc. in addition to the compounds represented by the formula (1) and exemplified above.

The living radical polymerization initiator represented by the formula (4) can be prepared by the same process as the compound of the formula (1) with the exception of using a compound represented by the formula (7) in place of the compound represented by the formula (3)

wherein $R^5$, M and m are as defined above.

Examples of compounds (7) usable are phenyllithium, p-chlorophenyllithium, p-methoxyphenyllithium, p-nitrophenyllithium, etc. in addition to the compounds (3). Phenyllithium is preferable.

The vinyl monomer to be used in the present invention is not particularly limited insofar as the monomer can be subjected to radical polymerization. Examples of vinyl monomers usable are methyl(meth)acrylate, ethyl(meth)acrylate, propyl(meth)acrylate, butyl(meth)acrylate, octyl(meth)acrylate, lauryl(meth)acrylate and like (meth)acrylic acid esters, cyclohexyl(meth)acrylate, methylcyclohexyl(meth)acrylate, isobornyl(meth)acrylate, cyclododecyl(meth)acrylate and like cycloalkyl-containing unsaturated monomers, (meth)acrylic acid, maleic acid, fumaric acid, itaconic acid, citraconic acid, crontonic acid, maleic anhydride and like carboxyl-containing unsaturated monomers, N,N-dimethylaminopropyl(meth)acrylamide, N,N-dimethylaminoethyl(meth)acrylamide, 2-(dimethylamino)ethyl(meth)acrylate, N,N-dimethylaminopropyl(meth)acrylate and like unsaturated monomers containing a tertiary amine, N-2-hydroxy-3-acryloyloxypropyl-N,N,N-trimethylammonium chloride, N-methacryloylaminoethyl-N,N,N-dimethylbenzylammonium chloride and like unsaturated monomers containing quaternary ammonium base, glycidyl (meth)acrylate and like epoxy-containing unsaturated monomers, styrene, α-methylstyrene, 4-methylstyrene, 2-methylstyrene, 3-methylstyrene, 4-methoxystyrene, 2-hydroxymethylstyrene, 2-chlorostyrene, 4-chlorostyrene, 2,4-dichlorostyrene, 1-vinylnaphthalene, divinylbenzene, p-styrenesulfonic acid or an alkali metal salt thereof (sodium salt or potassium salt, etc.) and like aromatic unsaturated monomers, 2-vinylthiophene, N-methyl-2-vinylpyrrole and like unsaturated monomers containing a heterocyclic ring, N-vinylformaldehyde, N-vinylacetamide and like vinylamides, 1-hexane, 1-octene, 1-decene and like α-olefins, vinyl acetate, hydroxyethyl methacrylate, acrylonitrile, acrylamide, N,N-dimethylacrylamide, vinyl chloride, etc.

Preferable among these are (meth)acrylic acid ester monomers, unsaturated monomers containing a tertiary amine, styrene monomers, acrylamide and N,N-dimethylacrylamide.

Examples of preferable (meth)acrylic acid ester monomers are methyl(meth)acrylate, ethyl(meth)acrylate, propyl(meth)acrylate and butyl(meth)acrylate. Especially preferable are methyl(meth)acrylate and butyl(meth)acrylate.

Examples of preferable unsaturated monomers containing a tertiary amine are N,N-dimethylaminoethyl(meth)acrylamide and 2-(dimethylamino)ethyl(meth)acrylate.

Examples of preferable styrene monomers are styrene, α-methylstyrene, o-methylstyrene, p-methylstyrene, p-methoxystyrene, p-t-butylstyrene, p-n-butylstyrene p-chlorostyrene, and p-styrenesulfonic acid or an alkali metal salt thereof (sodium salt or potassium salt, etc.). More preferable are styrene, p-methoxysytrene and p-chlorostyrene. The term "(meth)acrylic acid" refers collectively to "acrylic acid" and "methacrylic acid."

Next, a detailed description will be given of the process for preparing a polymer.

A vinyl monomer and a living radical polymerization initiator represented by the formula (4) are mixed together in a container with the air therein replaced by an inert gas. The inert gas to be used is, for example, nitrogen, argon, helium or the like. Preferable are argon and nitrogen. Nitrogen is more preferable. While the amounts of the vinyl monomer and the living radical polymerization initiator may be suitably adjusted in accordance with the molecular weight or molecular weight distribution of the living radical polymer to be obtained, usually 5 to 10,000 equivalents, preferably 50 to 5,000 equivalents, of the vinyl monomer is used per equivalent of the initiator. Although the reaction is conducted in the absence of solvent, a solvent may be used which is generally used for radical polymerization. Examples of solvents usable are benzene, toluene, N,N-dimethylformamide (DMF), dimethyl sulfoxide (DMSO), acetone, chloroform, carbon tetrachloride, tetrahydrofuran (THF), ethyl acetate, etc. DMF is preferred. While the amount of solvent to be used may be adjusted suitably, 0.01 to 1 ml, preferably 0.05 to 0.5 ml of solvent is used per gram of vinyl monomer.

The mixture is then stirred. The reaction temperature and the reaction time may be adjusted suitably in accordance with the molecular weight or molecular weight distribution of the living radical polymer to be obtained. The mixture is stirred usually at 60 to 150° C. for 5 to 100 hours, preferably at 80 to 120° C. for 10 to 30 hours. The reaction is conducted usually under atmospheric pressure, but may be conducted at increased pressure or in a vacuum.

After the completion of the reaction, the solvent used and the remaining monomer are removed in a vacuum to take out the desired polymer, or the desired product is isolated by re-precipitation using a solvent wherein the product is insoluble. The reaction mixture can be treated by any method insofar as it causes no problem to the desired product.

The living radical polymerization initiator of the present invention is adapted for excellent control of molecular weights and molecular weight distributions under very mild conditions.

The living radical polymer to be obtained by the invention is adjustable in molecular weight according to the reaction time and the amount of organotellurium compound, and can be 500 to 1,000,000 in number average molecular weight. The invention is especially suitable for producing living radical polymers having a number average molecular weight of 1,000 to 50,000.

The living radical polymer to be obtained by the invention is controlled to 1.05 to 1.50 in molecular weight distribution (PD=Mw/Mn). The molecular weight distribution is controllable to a narrower range of 1.05 to 1.30, a further narrower range of 1.05 to 1.20, a still narrower range of 1.05 to 1.15.

It has been found that the living radical polymer of the present invention has a terminal group which is an alkyl, aryl, substituted aryl, aromatic heterocyclic group, or hydroxycarbonyl derived from the organotellurium compound and a growth terminal which is highly reactive tellurium. Accordingly, the organotellurium compound used for radical polymerization makes it easier to convert the terminal group to other functional group than in the case of the living radical polymer obtained by conventional living radical polymerization. The living radical polymer obtained according to the invention is therefore usable as a macro living radical polymerization initiator (macroinitiator).

Stated more specifically, the use of the macro living radical polymerization initiator of the invention makes it possible to produce, for example, A—B diblock copolymers such as styrene-butyl acrylate, A—B—A triblock copolymers such as styrene-butyl acrylate-styrene and A—B—C triblock copolymers such as styrene-butyl acrylate-methyl methacrylate. This is attributable to the fact that the initiator of the present invention is capable of controlling various types of vinyl monomers and that highly reactive tellurium exists at the growth terminal of the living radical polymer to be obtained with use of the initiator.

Block copolymers can be produced by the processes to be described below in detail.

Like the process for producing the living radical polymer described above, A—B diblock copolymers such as styrene-butyl acrylate copolymer are produced by mixing together styrene and a living radical polymerization initiator of the invention represented by the formula (4) to obtain polystyrene first and subsequently mixing butyl acrylate with the polymer to obtain styrene-butyl acrylate copolymer.

A—B—A triblock copolymers or A—B—C triblock copolymers are produced by preparing an A—B diblock copolymer by the above process and thereafter mixing a vinyl monomer (A) or vinyl monomer (C) with the copolymer to obtain the triblock copolymer.

Each block prepared may be subjected as it is to the subsequent reaction to produce the next block, or the completion of the first reaction may be followed by purification and then by the subsequent reaction to obtain the next block. The block copolymer can be isolated by the usual method.

BEST MODE OF CARRYING OUT THE INVENTION

The present invention will be described below in detail with reference to Examples, but is not limited thereto in any way. In Examples and Comparative Examples, properties were determined by the following methods.

(1) Identification of Organotellurium Compounds and Living Radical Polymers

The organotellurium compound was identified based on the results of $^1$H-NMR, $^2$H-NMR, $^{13}$C-NMR, IR and MS analyses. The molecular weight and molecular weight distribution of the living radical polymer were determined with reference to the molecular weight of a polystyrene standard sample using GPC (gel permeation chromatography). The measuring instruments used are as follows.

$^1$H-NMR: Varian Gemini 2000 (300 MHz for $^1$H), JEOL JNM-A400 (400 MHz for $^1$H)

$^2$H-NMR: JEOL JNM-A400

$^{13}$C-NMR: Varian Gemini 2000, JEOL JNM-A400

IR: Shimadzu FTIR-8200 (cm$^{-1}$)

MS (HRMS, FAB-MS): JEOL JMS-300 molecular weight and molecular weight distribution: liquid chromatography Shimadzu LC-10 (column: Shodex K-804L+K-805L, polystyrene standard: TOSOH TSK Standard)

Preparation Example 1

Preparation of 1-(1-bromoethyl)-4-chlorobenzene [Compound (2) for Use in Example 2]

4-Chloroacetophenone (15.5 g, 100 mmoles) was dissolved in 100 ml of methanol, and a solution of 5.67 g (150 mmoles) of sodium borohydride in 250 ml of methanol was slowly added to the solution. The resulting solution was stirred overnight at room temperature. To the reaction mixture was added 1 N hydrochloric acid, and the organic layer was extracted with diethyl ether. The organic layer was collected and dried over anhydrous sodium sulfate, followed by concentration to obtain 1-(4-chlorophenyl)ethanol [$^1$H-NMR (300 MHz, CDCl$_3$) 1.48 (d, J=6.3 Hz, 3H), 4.88 (q, J=6.6 Hz, 1H), 7.31 (s, 4H)] in a nearly pure form.

To a solution of the above product 1-(4-chlorophenyl)ethanol in 100 ml of diethyl ether was slowly added a solution of 13.5 g (50 mmoles) of phosphorus tribromide in 50 ml of diethyl ether. The resulting solution was stirred overnight at room temperature. The reaction mixture was poured into ice water. Sodium hydrogencarbonate was added to the resulting solution for neutralization, and the organic layer was extracted with diethyl ether. The organic layer was collected, washed with water, dried over anhydrous sodium sulfate and concentrated in a vacuum, giving 9.00 g (41 mmoles, 82% in yield) of 1-(1-bromoethyl)-4-chlorobenzene [$^1$H-NMR (300 MHz, CDCl$_3$) 2.02 (d, J=6.9 Hz, 3H), 5.1 (q, J=6.9 Hz, 1H), 7.26-7.40 (m, 4H)] in a nearly pure form.

Preparation Example 2

Preparation of Phenyltrimethylsilyl Telluride (For Use in Comparative Example 1)

A 6.38 g quantity (50 mmoles) of metallic tellurium [product of Aldrich, brand name: Tellurium (–40 mesh)] was suspended in 50 ml of THF, and 52.8 ml of phenyllithium (product of Kanto Chemical Co., Ltd., brand name: Phenyllithium, cyclohexane-diethyl ether solution) was slowly added to the suspension at room temperature (for 15 minutes). The reaction mixture was stirred until the metallic tellurium disappeared completely (for 30 minutes). To the reaction mixture was added 5.98 g (55 mmoles) of trimethylsilyl chloride at room temperature, followed by stirring for 40 minutes. After the completion of reaction, the solvent was concentrated in a vacuum, followed by vacuum distillation to give 6.798 g (24.5 mmoles, 49% in yield) of yellow oil.

$^1$H-NMR analysis indicated that the product was phenyltrimethylsilyl telluride.

$^1$H-NMR (300 MHz, CDCl$_3$) 0.522 (s 9H), 7.095-7.144 (m, 2H), 7.245-7.312 (m, 1H), 7.220-7.758 (m, 2H)

Preparation Example 3

Preparation of 2-vinylthiophene (Vinyl Monomer for Use in Example 23)

Potassium tert-butoxide (20.2 g, 180 mmoles) was suspended in 200 ml of diethyl ether, and 64.3 g (180 mmoles) of methyltriphenyl phosphonium bromide was added to the suspension. The suspension, which was yellow, was refluxed for 1 hour. The mixture was cooled to room temperature, and 16.8 g (150 mmoles) of 2-thiophene aldehyde (stabilized with hydroquinone) was slowly added to the mixture at 0° C. (for 10 minutes), followed by refluxing for 1 hour. The reaction was completed by addition of water, the organic layer was extracted with ethyl acetate several times, and the organic layer collected was dried over anhydrous sodium sulfate and thereafter concentrated in a vacuum, affording 4.31 g (39.2 mmoles, 26% in yield) of clear oil.

$^1$H-NMR analysis indicated that the product was 2-vinylthiophene.

-NMR (300 MHz, CDCl$_3$) 5.41 (d, J=11.1 Hz, 1H), 5.57 (d, J=17.4 Hz, 1H), 6.81 (dd, J=17.3, 10.7 Hz, 1H), 6.94-7.00 (m, 2H), 7.24-7.20 (m, 1H)

Preparation Example 4

Preparation of N-methyl-2-vinylpyrrole (Vinyl Monomer for Use in Example 26)

Potassium tert-butoxide (13.5 g, 120 mmoles) was suspended in 200 ml of diethyl ether, and 42.9 g (120 mmoles) of methyltriphenyl phosphonium bromide was added to the suspension. The suspension, which was yellow, was refluxed for 1 hour. The mixture was cooled to room temperature, and 10.9 g (100 mmoles) of 1-methyl-2-pyrrole aldehyde was slowly added to the mixture at 0° C. (for 10 minutes), followed by refluxing for 1 hour. The reaction was completed by addition of water, the organic layer was extracted with ethyl acetate several times, and the organic layer collected was dried over anhydrous sodium sulfate and thereafter concentrated in a vacuum, affording 3.96 g (37.0 mmoles, 37% in yield) of clear oil.

$^1$H-NMR analysis indicated that the product was 1-methyl-2-vinylpyrrole.

$^1$H-NMR (300 MHz, CDCl$_3$) 3.62 (s, 3H), 5.04 (dd, J=11.3, 1.4 Hz, 1H), 5.47 (dd, J=17.4, 1.5 Hz, 1H), 6.07-6.14 (m, 1H), 6.37 (dd, J=3.6, 1.8 Hz, 1H), 6.52-6.66 (m, 2H)

Preparation Example 5

Preparation of ethyl-2-tributylstannylmethyl acrylate (For Use in Test Example 2)

To a solution of 1.5 ml (10.9 mmoles) of ethyl-2-bromomethyl acrylate in 22 ml of methanol was added 3.50 g (21.3 mmoles) of sodium benzenesulfinate, and the mixture was heated for refluxing for 11 hours. The solvent was distilled off in a vacuum, and water and ethyl acetate were added to the residue. The organic layer was separated off, and the aqueous layer was subjected to extraction with ethyl acetate three times. The combined organic layer was washed with a sodium chloride solution and dried with anhydrous sodium sulfate added thereto, the drying agent was filtered off, and the solvent was distilled off. The crude product obtained was purified by silica gel chromatography, giving 2.69 g of methyl-2-benzenesulfonylmethyl acrylate in a yield of 97%.

A solution of the methyl-2-benzenesulfonylmethyl acrylate (1.29 g, 5.1 mmoles) obtained 2.75 ml (10.2 mmoles) of tributyltin hydride and 33.4 mg (0.20 mmole) of azobisbutyronitrile (AIBN) in 2.6 ml of benzene was refluxed with heating for 1 hour. The solvent was distilled off, and the resulting product was purified by silica gel chromatography, giving 1.34 g of ethyl-2-tributylstannylmethyl acrylate in a yield of 65%.

Example 1

Preparation of (1-methyltellanyl-ethyl)benzene

A 6.38 g quantity (50 mmoles) of metallic tellurium (the same as above) was suspended in 50 ml of THF, and 52.9 ml (1.04 M diethyl ether solution, 55 mmoles) of methyllithium (product of Kanto Chemical Co., Ltd., brand name: Methyllithium, diethyl ether solution) was slowly added dropwise to the suspension at room temperature (for 10 minutes). The reaction mixture was stirred until the metallic tellurium disappeared completely (for 20 minutes). To the reaction mixture was added 11 g (60 mmoles) of (1-bromoethyl)benzene at room temperature, followed by stirring for 2 hours. After the completion of reaction, the solvent was concentrated in a vacuum, followed by vacuum distillation to give 8.66 g of yellow oil (70% in yield).

IR, MS (HRMS), $^1$H-NMR and $^{13}$C-NMR analyses indicated that the product was (1-methyltellanyl-ethyl)benzene.

IR (neat, cm$^{-1}$) 1599, 1493, 1451, 1375, 1219, 1140, 830, 760, 696, 577

HRMS (EI) m/z: Calcd for $C_9H_{12}Te(M)^+$, 250.0001; Found 250.0001

$^1$H-NMR (300 MHz, CDCl$_3$) 1.78 (s, 3H, TeCH$_3$), 1.90 (d, J=7.2 Hz, 3H), 4.57 (q, J=7.2 Hz, 1H, CHTe), 7.08-7.32 (m, 5H)

$^{13}$C-NMR (75 MHz, CDCl$_3$) −18.94, 18.30, 23.89, 126.17, 126.80, 128.30, 145.79

Example 2

Preparation of 1-chloro-4-(1-methyltellanyl-ethyl)benzene

A 4.08 g quantity (32 mmoles) of metallic tellurium was suspended in 50 ml of THF, and 42 ml (35 mmoles) of methyllithium (the same as above) was slowly added dropwise to the suspension at 0° C. (for 20 minutes). The reaction mixture was stirred until the metallic tellurium disappeared completely (for 10 minutes). To the reaction mixture was added 7.68 g (35 mmoles) of 1-(1-bromoethyl)-4-chlorobenzene (obtained in Preparation Example 1) at room temperature, followed by stirring for 1.5 hours. After the completion of reaction, the solvent was concentrated in a vacuum, followed by vacuum distillation to give 3.59 g (12.7 mmoles, 36% in yield) of brown oil.

$^1$H-NMR and $^{13}$C-NMR analyses indicated that the product was 1-chloro-4-(1-methyltellanyl-ethyl)benzene.

$^1$H-NMR (300 MHz, CDCl$_3$), 1.81 (s, 3H, TeCH$_3$), 1.89 (d, J=6.6 Hz, 3H), 4.54 (q, J=7.2 Hz, 1H), 7.23 (s, 4H)

$^{13}$C-NMR (100 MHz, CDCl$_3$) −18.80 (TeCH$_3$), 17.18 (CH$_3$), 23.81 (CH), 128.08 (CH, 2C), 128.39 (CH, 2C), 131.15 (C), 144.45 (C)

Example 3

Preparation of (1-phenyltellanyl-ethyl)benzene

The same procedure as in Example 1 was performed with the exception of using 53.0 ml (1.06 M diethyl ether solution, 55 mmoles) of phenyllithium (same as above) in place of methyllithium to obtain 1.53 g (10% in yield) of yellow oil.

MS (HRMS) and $^1$H-NMR analyses indicated that the product was (1-phenyltellanyl-ethyl)benzene.

HRMS (EI) m/z: Calcd for $C_{14}H_{14}Te(M)^+$, 312.0158; Found 312.0164

$^1$H-NMR (300 MHz, CDCl$_3$) 1.97 (d, J=7.5 Hz, 3H), 4.80 (q, J=7.2 Hz, 1H, CHTe), 7.00-7.71 (m, 10H)

Example 4

Preparation of (methyltellanyl-methyl)benzene

The same procedure as in Example 1 was performed with the exception of using 9.4 g (55 mmoles) of benzyl bromide in place of (1-bromoethyl)benzene to obtain 7.30 g (50% in yield) of yellow oil.

MS (HRMS), $^1$H-NMR and $^{13}$C-NMR analyses indicated that the product was (methyltellanyl-methyl)benzene.

IR (neat, cm$^{-1}$) 1599, 1493, 1453, 1418, 1221, 1140, 1059, 1030, 847, 754, 696, 569

HRMS (EI) m/z: Calcd for $C_8H_{10}Te(M)^+$, 235.9845; Found 235.9844

$^1$H-NMR (300 MHz, CDCl$_3$) 1.83 (s, 3H, TeCH$_3$), 3.97 (s, 2H), 7.10-7.32 (m, 5H)

$^{13}$C NMR (75 MHz, CDCl$_3$) −18.48, 37.86, 125.81, 128.29, 140.89, 141.67

Example 5

Preparation of ethyl-2-methyl-2-methyltellanyl-propionate

The same procedure as in Example 1 was performed with the exception of using 10.7 g (55 mmoles) of ethyl-2-bromoisobutyrate in place of (1-bromoethyl)benzene to obtain 6.53 g (51% in yield) of yellow oil.

IR, MS (HRMS), $^1$H-NMR and $^{13}$C-NMR analyses indicated that the product was ethyl-2-methyl-2-methyltellanyl-propionate.

IR (neat, cm$^{-1}$) 1700, 1466, 1385, 1269, 1146, 1111, 1028

HRMS (EI) m/z: Calcd for $C_7H_{14}O_2Te(M)^+$, 260.0056; Found 260.0053

$^1$H-NMR (300 MHz, CDCl$_3$) 1.27 (t, J=6.9 Hz, 3H), 1.74 (s, 6H), 2.15 (s, 3H, TeCH$_3$), 4.16 (q, J=7.2 Hz, 2H)

$^{13}$C-NMR (75 MHz, CDCl$_3$) −17.38, 13.89, 23.42, 27.93, 60.80, 176.75

Example 6

Preparation of 2-methyltellanylpropionitrile

A 6.38 g quantity (50 mmoles) of metallic tellurium was suspended in 50 ml of THF, and 52.9 ml (55 mmoles) of methyllithium was slowly added dropwise to the suspension at room temperature (for 10 minutes). The reaction mixture was stirred until the metallic tellurium disappeared completely (for 20 minutes). To the reaction mixture was added 8.0 g (60 mmoles) of 2-bromopropionitrile at room temperature, followed by stirring for 2 hours. After the completion of reaction, the solvent was concentrated in a vacuum, followed by vacuum distillation to give 4.52 g (46% in yield) of yellow oil.

IR, MS (HRMS), $^1$H-NMR and $^{13}$C-NMR analyses indicated that the product was 2-methyltellanylpropionitrile.

Comparative Example 1

Preparation of (diphenyl-phenyltellanyl-methoxy)trimethylsilane

Benzophenone (0.92 g, 5.0 mmoles) was dissolved in 5.0 ml of propionitrile, and 1.39 g (5.0 mmoles) of phenyltrimethylsilyl telluride (obtained in Preparation Example 2) was slowly added dropwise to the solution at room temperature, followed by stirring for 12 hours. After the completion of reaction, a pink power precipitate was filtered off, washed with cold hexane and then dried in a vacuum to obtain 1.37 g of the above substance (60% in yield). The filtrate was concentrated, and the solid residue was recrystallized from propionitrile/hexane/ethyl acetate for purification to obtain 0.63 g (29%) of a second product.

IR, MS (FAB-MS), $^1$H-NMR and $^{13}$C-NMR analyses indicated that the product was (diphenyl-phenyltellanyl-methoxy)trimethylsilane. Melting point 65.3-66.4° C.

IR (KBr) 1265 (m), 1250 (m), 1170 (m), 1110 (s), 1075 (m), 870 (s), 835 (s), 750 (m), 735 (m), 720 (m), 700 (s), 690 (m)

$^1$H-NMR (300 MHz, CDCl$_3$) –0.02 (s, 9H), 7.05-7.25 (m, 13H), 7.81-7.84 (m, 2H)

$^{13}$C-NMR (75 MHz, CDCl$_3$) 2.3, 88.4, 108.0, 125.8, 126.4, 128.2, 129.4 131.2, 137.7, 145.8

FAB-MS (matrix: 3-nitrobenzylalcohol) m/z: 255 (M-TePh)$^+$

Comparative Example 2

Preparation of tellurium-methyltellurobenzoate

A 6.38 g quantity (50 mmoles) of metallic tellurium (the same as above) was suspended in 50 ml of THF, and 48.0 ml (1.14 M diethyl ether solution, 55 mmoles) of methyllithium (the same as above) was slowly added dropwise to the suspension at room temperature (for 20 minutes). To the reaction mixture was added 7.7 g (55 mmoles) of benzoyl chloride at 0° C., and the resulting mixture was stirred at room temperature for 30 minutes. After the completion of reaction, the solvent was concentrated in a vacuum, followed by vacuum distillation to give 8.75 g of red oil (71% in yield).

IR, MS (HRMS), $^1$H-NMR and $^{13}$C-NMR analyses indicated that the product was tellurium-methyltellurobenzoate.

IR (neat, cm$^{-1}$) 1660, 1580, 1447, 1200, 1169, 868, 762, 685, 666, 596

HRMS (EI) m/z: Calcd for C$_8$H$_8$OTe(M)$^+$, 249.9637; Found 249.9635

$^1$H-NMR (300 MHz, CDCl$_3$) 2.25 (s, 3H, TeCH$_3$), 7.41 (t, J=6.9 Hz, 2H), 7.57 (t, J=7.7 Hz, 1H), 7.70-7.78 (m, 2H)

$^{13}$C-NMR (75 MHz, CDCl$_3$) –14.72, 126.63, 128.79, 133.59, 142.67, 195.64

Examples 7 to 13

Living Radical Polymerization of Styrene

Prepared as listed in Table 1 in a glove box containing nitrogen in place of air was a mixture of styrene and 24.8 mg (0.10 mmole) of the (1-methyltellanyl-ethyl)benzene prepared in Example 1, followed by reaction at 105° C. for 18 to 29 hours. After the completion of reaction, the mixture was dissolved in 5 ml of chloroform, and the solution was then poured into 250 ml of methanol which was being stirred. A polymer precipitate was aspirated for filtration and dried to obtain a polystyrene. Table 1 shows the result obtained by GPC analysis.

TABLE 1

|  | styrene (equivalent) | reaction time (h) | yield (%) | Mn | PD |
| --- | --- | --- | --- | --- | --- |
| Example 7 | 100 | 18 | 96 | 9200 | 1.17 |
| Example 8 | 200 | 20 | 87 | 18400 | 1.18 |
| Example 9 | 300 | 23 | 85 | 25200 | 1.22 |
| Example 10 | 400 | 27 | 78 | 29500 | 1.17 |
| Example 11 | 500 | 27 | 78 | 35700 | 1.21 |
| Example 12 | 800 | 27 | 80 | 52600 | 1.30 |
| Example 13 | 1000 | 29 | 84 | 62600 | 1.37 |

Example 14

Styrene (1.04 g, 10 mmoles) and 30.9 mg (0.16 mmole) of the (1-phenyltellanyl-ethyl)benzene prepared in Example 3 were mixed together within a glove box containing nitrogen in place of air, and reacted at 105° C. for 17 hours. After the completion of reaction, the mixture was dissolved in 5 ml of chloroform, and the solution was then poured into 200 ml of methanol which was being stirred. A polymer precipitate was aspirated for filtration and dried, to obtain 0.9481 g (91% in yield) of a polystyrene. GPC analysis revealed Mn 15900 and PD=1.45.

Example 15

Styrene (1.04 g, 10 mmoles) and 23.4 mg (0.10 mmole) of the (methyltellanyl-methyl)benzene prepared in Example 4 were mixed together within a glove box containing nitrogen in place of air, and reacted at 105° C. for 16 hours. After the completion of reaction, the mixture was dissolved in 5 ml of chloroform, and the solution was then poured into 250 ml of methanol which was being stirred. A polymer precipitate was aspirated for filtration and dried, to obtain 0.9273 g (89% in yield) of a polystyrene. GPC analysis revealed Mn 9000 and PD=1.46.

Example 16

Styrene (1.04 g, 10 mmoles) and 25.8 mg (0.10 mmole) of the ethyl-2-methyl-2-methyltellanyl-propionate prepared in Example 5 were mixed together within a glove box containing nitrogen in place of air, and reacted at 105° C. for 20 hours. After the completion of reaction, the mixture was dissolved in 5 ml of chloroform, and the solution was then poured into 250 ml of methanol which was being stirred. A polymer precipitate was aspirated for filtration and dried, to obtain 0.9286 g (89% in yield) of a polystyrene. GPC analysis revealed Mn 9000 and PD=1.46.

Example 17

Styrene (1.04 g, 10 mmoles) and 19.7 mg (0.10 mmole) of the 2-methyltellanylpropionitrile prepared in Example 6 were mixed together within a glove box containing nitrogen in place of air, and reacted at 100° C. for 11 hours. After the completion of reaction, the mixture was dissolved in 5 ml of chloroform, and the solution was then poured into 250 ml of hexane which was being stirred. A polymer precipitate was aspirated for filtration and dried, to obtain 1.01 g (97% in yield) of a polystyrene. GPC analysis revealed Mn 11000 and PD=1.21.

Example 18 p-Chlorostyrene (1.39 g, 10 mmoles) and 24.8 mg (0.10 mmole) of the (1-methyltellanyl-ethyl)benzene prepared in Example 1 were mixed together within a glove box containing nitrogen in place of air, and reacted at 100° C. for 17 hours. After the completion of reaction, the mixture was dissolved in 5 ml of chloroform, and the solution was then poured into 250 ml of methanol which was being stirred. A polymer precipitate was aspirated for filtration and dried, to obtain 1.2244 g (88% in yield) of a poly-p-chlorostyrene. GPC analysis revealed Mn 8800 and PD=1.41.

Example 19 p-Methoxystyrene (1.18 g, 10 mmoles) and 24.8 mg (0.10 mmole) of the (1-methyltellanyl-ethyl)benzene prepared in Example 1 were mixed together within a glove box containing nitrogen in place of air, and reacted at 105° C. for 13 hours. After the completion of reaction, the mixture was dissolved in 5 ml of chloroform, and the solution was then poured into 250 ml of methanol which was being stirred. A polymer precipitate was aspirated for filtration and dried, to obtain 1.1018 g (93% in yield) of a poly-p-methoxystyrene. GPC analysis revealed Mn 10600 and PD=1.13.

Comparative Example 3

Styrene (1.04 g, 10 mmoles) and 46.0 mg (0.10 mmole) of the (diphenyl-phenyltellanyl-methoxy)trimethylsilane prepared in Comparative Example 1 were mixed together within a glove box containing nitrogen in place of air, and reacted at 105° C. for 16 hours. After the completion of reaction, the mixture was dissolved in 5 ml of chloroform, and the solution was then poured into 250 ml of methanol which was being stirred. A polymer precipitate was aspirated for filtration and dried, to obtain 0.7875 g (76% in yield) of a polystyrene. GPC analysis revealed Mn 50700 and PD=1.80.

Comparative Example 4

Styrene (1.04 g, 10 mmoles) and 24.8 mg (0.10 mmole) of the tellurium-methyltellurobenzoate prepared in Comparative Example 2 were mixed together within a glove box containing nitrogen in place of air, and reacted at 105° C. for 18 hours. After the completion of reaction, the mixture was dissolved in 5 ml of chloroform, and the solution was then poured into 250 ml of methanol which was being stirred. A polymer precipitate was aspirated for filtration and dried, to obtain 0.8660 g (83% in yield) of a polystyrene. GPC analysis revealed Mn 25400 and PD=1.58.

Example 20

Methyl acrylate stabilized with hydroquinone methyl ether (MEHQ) (8.60 g, 10 mmoles) and 24.8 mg (0.10 mmole) of the (1-methyltellanyl-ethyl)benzene prepared in Example 1 were mixed together within a glove box containing nitrogen in place of air, and reacted at 100° C. for 24 hours. After the completion of reaction, the mixture was dissolved in 5 ml of chloroform, and the solution was then poured into 250 ml of hexane which was being stirred. A polymer precipitate was aspirated for filtration and dried, to obtain 7.40 g (86% in yield) of a polymethyl acrylate. GPC analysis revealed Mn 8800 and PD=1.12.

Example 21

Methyl acrylate (8.60 g, 10 mmoles) and 25.8 mg (0.10 mmole) of the ethyl-2-methyl-2-methyltellanyl-propionate prepared in Example 5 were mixed together within a glove box containing nitrogen in place of air, and reacted at 100° C. for 24 hours. After the completion of reaction, the mixture was dissolved in 5 ml of chloroform, and the solution was then poured into 250 ml of hexane which was being stirred. A polymer precipitate was aspirated for filtration and dried, to obtain 6.03 g (70% in yield) of a polymethyl acrylate. GPC analysis revealed Mn 6400 and PD=1.11.

Example 22 n-Butyl acrylate stabilized with MEHQ (1.28 g, 10 mmoles) and 24.8 mg (0.10 mmole) of the (1-methyltellanyl-ethyl)benzene prepared in Example 1 were mixed together within a glove box containing nitrogen in place of air, and reacted at 100° C. for 24 hours. After the completion of reaction, the mixture was dissolved in 5 ml of chloroform, and the solution was then poured into 250 ml of hexane which was being stirred. A polymer precipitate was aspirated for filtration and dried, to obtain 1.15 g (89% in yield) of a poly-n-butyl acrylate. GPC analysis revealed Mn 10300 and PD=1.13.

Example 23

N,N-dimethylacrylamide stabilized with MEHQ (0.99 g, 10 mmoles) and 24.8 mg (0.10 mmole) of the (1-methyltellanyl-ethyl)benzene prepared in Example 1 were mixed together within a glove box containing nitrogen in place of air, and reacted at 100° C. for 19 hours. After the completion of reaction, the mixture was dissolved in 5 ml of chloroform, and the solution was then poured into 250 ml of hexane which was being stirred. A polymer precipitate was aspirated for filtration and dried, to obtain 0.92 g (93% in yield) of a poly-N,N-dimethylacrylamide. GPC analysis revealed Mn 10600 and PD=1.26.

Example 24

2-(Dimethylamino)ethyl acrylate stabilized with MEHQ (14.3 g, 10 mmoles) and 24.8 mg (0.10 mmole) of the (1-methyltellanyl-ethyl)benzene prepared in Example 1 were dissolved in 1 ml of DMF and the solution was reacted at 100° C. for 96 hours within a glove box containing nitrogen in place of air. After the completion of reaction, the solvent was removed by distillation under reduced pressure to obtain 11.583 g (81% in yield) of a poly-2-(dimethylamino)ethyl acrylate. GPC analysis revealed Mn 12000 and PD=1.23.

Example 25

2-Vinylthiophene obtained in Preparation Example 3 (1.10 g, 10 mmoles) and 24.8 mg (0.10 mmole) of the (1-methyltellanyl-ethyl)benzene prepared in Example 1 were mixed together within a glove box containing nitrogen in place of air, and reacted at 100° C. for 15 hours. After the completion of reaction, the mixture was dissolved in 5 ml of chloroform, and the solution was then poured into 250 ml of hexane which was being stirred A polymer precipitate was aspirated for filtration and dried, to obtain 1.08 g (97% in yield) of a poly-2-vinylthiophene. GPC analysis revealed Mn 9500 and PD=1.25.

Example 26

2-Vinylthiophene (same as above) (1.10 g, 10 mmoles) and 25.8 mg (0.10 mmole) of the ethyl-2-methyl-2-methyltellanyl-propionate prepared in Example 5 were mixed together within a glove box containing nitrogen in place of air, and reacted at 100° C. for 15 hours. After the completion of reaction, the mixture was dissolved in 5 ml of chloroform, and the solution was then poured into 250 ml of hexane which was being stirred. A polymer precipitate was aspirated for filtration and dried, to obtain 1.04 g (95% in yield) of a poly-2-vinylthiophene. GPC analysis revealed Mn 7600 and PD=1.34.

Example 27

N-Methyl-2-vinylpyrrole obtained in Preparation Example 4 (1.07 g, 10 mmoles) and 24.8 mg (0.10 mmole) of the (1-methyltellanyl-ethyl)benzene prepared in Example 1 were mixed together within a glove box containing nitrogen in place of air, and reacted at 100° C. for 20 hours. After the completion of reaction, the mixture was dissolved in 5 ml of chloroform, and the solution was then poured into 250 ml of hexane which was being stirred. A polymer precipitate was aspirated for filtration and dried, to obtain 1.02 g (95% in yield) of a poly-N-methyl-2-vinylpyrrole. GPC analysis revealed Mn 12700 and PD=1.15.

Example 28

N-Methyl-2-vinylpyrrole (same as above) (1.10 g, 10 mmoles) and 25.8 mg (0.10 mmole) of the ethyl-2-methyl-2-methyltellanyl-propionate prepared in Example 5 were mixed together within a glove box containing nitrogen in place of air, and reacted at 100° C. for 20 hours. After the completion of reaction, the mixture was dissolved in 5 ml of chloroform, and the solution was then poured into 250 ml of hexane which was being stirred. A polymer precipitate was aspirated for filtration and dried, to obtain 1.05 g (96% in yield) of a poly-N-methyl-2-vinylpyrrole. GPC analysis revealed Mn 13800 and PD=1.12.

Example 29

Synthesis of Poly(styrene-b-tert-butyl acrylate) diblock polymer

Styrene (1.04 g, 10 mmoles) and 24.8 mg (0.10 mmole) of the (1-methyltellanyl-ethyl)benzene prepared in Example 1 were reacted within a glove box containing nitrogen in place of air at 100° C. for 20 hours. After the completion of reaction, the mixture was dissolved in 5 ml of chloroform-d, and the solution was then poured into 300 ml of methanol which was being stirred. A polymer precipitate was aspirated for filtration and dried, to obtain 1.015 g (95% in yield) of a polystyrene. GPC analysis revealed Mn 9000 and PD=1.15.

Next, 521 mg (0.05 mmole) of the polystyrene (for use as an initiator) obtained above and 640 mg (5 mmoles) of tert-butyl acrylate (stabilized with MEHQ) were reacted at 100° C. for 25 hours. After the completion of reaction, the reaction mixture was dissolved in 5 ml of chloroform, and the solution was then poured into 300 ml of a mixture solution of water and methanol (water:methanol=1:4). A polymer precipitate was aspirated for filtration, and dried, giving 580 mg (50% in yield) of poly(styrene-b-tert-butyl acrylate) diblock polymer. GPC analysis revealed Mn 11300 and PD=1.18.

Test Example 1

Marking Experiment of Polystyrene Terminal Group (Heavy Hydrogen Conversion)

Styrene (1.04 g, 10 mmoles) and 24.8 mg (0.10 mmole) of the (1-methyltellanyl-ethyl)benzene prepared in Example 1 and serving as an initiator were mixed together within a glove box containing nitrogen in place of air, and reacted at 105° C. for 19 hours. The reaction mixture was dissolved in 4 ml of THF, 87.6 mg (0.30 mmole) of tributyltin heavy hydrogen and 1.6 mg (0.01 mmole) of azobisbutyronitrile (AIBN) were added to the solution, and the mixture was reacted at 80° C. for 4 hours. After the completion of reaction, the reaction mixture was poured into 250 ml of methanol which was being stirred. A polymer precipitate was obtained by aspiration. Analyzing GPC (gel permeation chromatography) indicated that the polymer obtained was 8500 in Mn, 1.18 in PD and 82% in yield. The polymer was purified by fractionating GPC. $^2$H-NMR analysis with use of tetrachloroethane-d$_2$ indicated that the benzyl position had been converted to heavy hydrogen atoms at least 93%.

Test Example 2

Conversion of Polystyrene Terminal Group to α,β-Unsaturated Ester

Styrene (1.04 g, 10 mmoles) and 24.8 mg (0.10 mmole) of the (1-methyltellanyl-ethyl)benzene prepared in Example 1 and serving as an initiator were mixed together within a glove box containing nitrogen in place of air and stirred at 105° C. for 14 hours. The reaction mixture was dissolved in 4 ml of THF, 161.3 mg (0.40 mmole) of ethyl-2-tributylstannylmethyl acrylate and 1.6 mg (0.01 mmole) of AIBN were added to the solution, and the mixture was reacted at 80° C. for 6 hours. After the completion of reaction, the reaction mixture was poured into 250 ml of methanol which was being stirred. A polymer precipitate was obtained by aspiration. Fractionating GPC gave a polymer which was found to be 10000 in Mn, 1.16 in PD and 93% in yield. $^1$H-NMR analysis indicated that the polymer terminal group had been converted to an acrylic ester group 61%.

Test Example 3

Conversion of Polystyrene Terminal Group to Lithium Carboxylate

Styrene (2.08 g, 20 mmoles) and 49.6 mg (0.20 mmole) of the (1-methyltellanyl-ethyl)benzene prepared in Example 1 and serving as an initiator were mixed together within a glove box containing nitrogen in place of air and stirred at 105° C.

for 18 hours. The reaction mixture was dissolved in 10 ml of THF, and 0.20 ml of n-butyllithium (1.48 M hexane solution, 0.30 mmole, product of Kanto Chemical Co., Ltd., brand name: n-Butyllithium, hexane solution) was added to the solution at −78° C., whereupon the color of the solution changed from yellow to red. The mixture was stirred at the same temperature for 3 minutes, carbon dioxide was forced into the mixture for 1 minute, and a transparent solution obtained was treated with 19.2 mg (0.60 mmole) of methanol. The resulting mixture was returned to room temperature. After the completion of reaction, the reaction mixture was washed with water, and the aqueous layer was subjected to extraction with Et$_2$O three times. An organic layer was collected, dried over anhydrous sodium sulfate and thereafter concentrated in a vacuum. The concentrate was purified by re-precipitation to obtain a polystyrene having a carboxylated terminal group. The polymer was 92% (1.922 g) in yield, 10400 in Mn and 1.18 in PD.

Test Example 4

Conversion of Polystyrene Terminal Group to Pyrene Ester

To a solution of 832 mg (0.08 mmole) of the polystyrene (10400 in Mn and 1.18 in PD) having a lithium carboxylated terminal group and prepared in Test Example 3 in 4 ml of THF were added 16.2 mg (0.16 mmole) of triethylamine and 39 mg (0.16 mmole) of 2,4,6-trichlorobenzoyl chloride, and the mixture was reacted at room temperature for 1.5 hours. Volatile substances (chiefly THF) were evaporated off in a vacuum, and 87.8 mg (0.32 mmole) of 1-pyrenebutanol, 39.1 mg (0.32 mmole) of 4-dimethylaminopyridine (DMAP) and 5 ml of dichloromethane were added to the residue. The mixture was stirred at room temperature for 3 hours, the reaction mixture was poured into methanol which was being stirred, and a polymer precipitate was obtained by aspiration. The polymer was purified by fractionating GPC, followed by re-precipitation with chloroform and methanol to obtain 812 mg of a polymer. UV measurement (λ=344 nm) and HPLC analysis revealed that the polymer had its terminal group converted 86%.

INDUSTRIAL APPLICABILITY

The invention provides organotellurium compounds and a process for preparing the same. The organotellurium compound is useful as a living radical polymerization initiator and adapted for precision control of molecular weights and molecular weight distributions under mild conditions. Living radical polymers obtained by polymerization have a terminal group which can be readily converted to other functional group. The living radical polymer obtained by the invention can therefore be used as a macro living radical polymerization initiator (macroinitiator).

The invention claimed is:

1. A living radical polymer which is obtained by subjecting a vinyl monomer to living radical polymerization with use of a living radical polymerization initiator of the formula (4)

wherein $R^1$ is $C_1$-$C_8$ alkyl, $R^2$ and $R^3$ are each a hydrogen atom or $C_1$-$C_8$ alkyl, and $R^4$ is aryl, substituted aryl, aromatic heterocyclic group, hydroxycarbonyl or cyano.

2. A macro living radical polymerization initiator comprising the living radical polymer of claim 1.

3. A process for producing a block copolymer comprising polymerizing a vinyl monomer using the macro living radical polymerization initiator of claim 2 as a living radical polymerization initiator.

4. A block copolymer which is obtained by polymerizing a vinyl monomer using the macro living radical polymerization initiator of claim 2 as a living radical polymerization initiator.

5. A living radical polymer as defined in claim 1 which is obtained by subjecting a vinyl monomer to living radical polymerization with use of a living radical polymerization initiator of the formula (6)

wherein $R^5$ is $C_1$-$C_8$ alkyl, aryl, substituted aryl or aromatic heterocyclic group, $R^2$ and $R^3$ are each a hydrogen atom or $C_1$-$C_8$ alkyl, and $R^4$ is cyano.

6. A macro living radical polymerization initiator comprising the living radical polymer of claim 5.

7. A process for producing a block copolymer comprising polymerizing a vinyl monomer using the macro living radical polymerization initiator of claim 6 as a living radical polymerization initiator.

8. A block copolymer which is obtained by polymerizing a vinyl monomer using the macro living radical polymerization initiator of claim 6 as a living radical polymerization initiator.

9. A process for producing a block copolymer comprising polymerizing a vinyl monomer using the macro living radical polymerization initiator for preparing a block copolymer of claim 2 as a living radical polymerization initiator.

10. A block copolymer which is obtained by polymerizing a vinyl monomer using the macro living radical polymerization initiator for preparing a block copolymer of claim 2 as a living radical polymerization initiator.

11. A macro living radical polymerization initiator for preparing a block copolymer comprising the living radical polymer of claim 5.

* * * * *